United States Patent [19]
Cowan

[11] Patent Number: 5,947,991
[45] Date of Patent: Sep. 7, 1999

[54] SINGLE BALLOON DEVICE FOR CERVIX

[76] Inventor: Robert K. Cowan, 1015 E. 32$^{nd}$ St., Suite 516, Austin, Tex. 78705

[21] Appl. No.: 08/780,434

[22] Filed: Jan. 7, 1997

[51] Int. Cl.$^6$ .................................................. A61M 29/00
[52] U.S. Cl. .............................. 606/191; 604/96; 606/193
[58] Field of Search ............................ 604/96, 101, 265; 606/191, 192, 193; 128/832

[56] References Cited

U.S. PATENT DOCUMENTS

| | | | |
|---|---|---|---|
| 2,499,045 | 2/1950 | Walker et al. | 606/192 |
| 3,045,677 | 7/1962 | Wallace | 606/192 |
| 4,687,471 | 8/1987 | Twardowski et al. | |
| 4,772,269 | 9/1988 | Twardowski et al. | |
| 4,976,692 | 12/1990 | Atad | |
| 5,104,377 | 4/1992 | Levine | 606/193 |
| 5,352,199 | 10/1994 | Tower | 604/96 |

FOREIGN PATENT DOCUMENTS

| | | | |
|---|---|---|---|
| 4012-642 | 10/1991 | Germany | 606/192 |

OTHER PUBLICATIONS

Atad, Jack, MD, et al. "Instruments & Methods", *Obstetrics & Gynecology*, vol. 77, No. 1, Jan. 1991.

Trofatter, Kenneth F., Jr., PhD, MD. "Cervical Ripening", *Clinical Obstetrics and Gynecology*, vol. 35, No. 3, Sep. 1992.

Rouben, Divya, MD and Fernando Arias, MD, PhD. "A Randomized Trial of Extra–Amniotic Saline Infusion Plus Intracervical Foley Catheter Balloon Versus Prostaglandin E$_2$ Vaginal Gel for Ripening the Cervix and Inducing Labor in Patients With Unfavorable Cervices", *Obstetrics & Gynecology*, vol. 82, No. 2, Aug. 1993.

James, C, et al. "Use of the Foley catheter as a cervical ripening agent prior to induction of labor", *International Journal of Gynecology & Obstetrics*, 57 (1994) 299–232.

St. Onge, Rick D., MD and Gregory T. Connors, MD. "Preinduction cervical ripening: A comparison of intracervical prostaglandin E$_2$ gel versus the Foley catheter", *American Journal of Obstetrics & Gynecology*, vol. 172, No. 2, Part 1, 1995.

Kauff, Noah D., et al. "Intractable bleeding managed with Foley catheter tamponade after dilation and evacuation", *American Journal of Obstetrics & Gynecology*, vol. 173, No. 3, Part 1, 1995.

Atad, Jack, MD, et al. "A Randomized Comparison of Prostaglandin E$_2$, Oxytocin, and the Double–Balloon Device in Inducing Labor", *Obstetrics & Gynecology*, vol. 87, No. 2, Feb. 1996.

*Primary Examiner*—Michael Buiz
*Assistant Examiner*—Julian W. Woo
*Attorney, Agent, or Firm*—Arnold, White & Durkee

[57] ABSTRACT

The present invention is an improved balloon catheter for cervical dilation having a shape when inflated that is larger in diameter at the portions of the balloon that extend into the cervix and vagina, and is narrower in diameter at the middle, or cervical portion. This improved shape of the inflated catheter allows an easier and simplified placement of the catheter in a patient and retention of the catheter in position during cervical dilation.

19 Claims, 1 Drawing Sheet

SINGLE BALLOON DEVICE FOR CERVIX

BACKGROUND OF THE INVENTION

Cervical ripening, or opening of the cervix prior to the onset of labor, is under hormonal control. Failure of the cervix to ripen at term increases the chance of delivery problems, including the need for cesarean section. Further consequences include prolonged hospital stays, increased medical costs, and an overall increase in maternal and fetal morbidity. There are several devices and methods presently utilized to induce artificially the ripening of the cervix to prevent pregnancy complications. One of the most widely used methods involves the intravenous administration of oxytocin. This method, however, causes a prolonged period of induction, tends to suffer from a large failure rate, and may cause patient discomfort. Other common methods of inducing labor include administration of prostaglandin (PG), either systemically or by topical application. Like oxytocin, PG may cause certain undesirable side effects, such as nausea, vomiting, and uterine hypertoxicity.

Mechanical methods of inducing ripening include the use of balloon catheters and hygroscopic cervical dilators. Such devices have the advantage of causing a gradual cervical dilation and minimizing patient discomfort. Several types of catheters have been utilized for this purpose. One example is that disclosed in U.S. Pat. No. 4,976,692 to Atad et al., showing a two balloon catheter that is placed such that one balloon is in the uterus, and the other balloon is in the vagina. Each balloon connects separately to flexible tubing, permitting independent filling or emptying of each balloon. This particular catheter also has a third flexible tube that allows injection of pharmaceutical agents through a gap between both balloons, or inside the cervix. However, this catheter requires manipulation and adjustment of three different valves arranged in a cumbersome fashion. Moreover, the administration of pharmaceutical agents in the cervical area through this catheter may fail to deliver the entire dose, as the agents must travel from the valve through the tube to the discharge site.

Thus, there is a need for a simple yet effective product to use in the ripening of the cervix and inducement of labor.

SUMMARY OF THE INVENTION

The present invention provides an improved single balloon catheter to induce cervical ripening. This catheter may be approximately 35 cm long, and 4 mm to 6 mm in diameter. When inflated, the hourglass shaped balloon has dimensions of about 6 to 8 cm in length, 5 cm in diameter at the end portions, and about 3 cm in diameter in the center portion, with a total volume of about 30–40 mL. Thus, the general shape of the balloon portion of the catheter is an hourglass or dumbbell shape, with two end portions that are larger in diameter than the central section, or central portion. The end portions which extend into the vagina and uterus are so shaped to hold the balloon in position.

The balloon and inflation tube are preferably constructed of biocompatible materials. Biocompatible materials for the balloon should be elastomeric in nature to allow expansion and contraction. These materials include, but are not limited to, latex, rubber including nitrile rubber, styrene butadiene rubber, viton, or butyl rubber, silicone, dacron-reinforced silicon material, polyethylene, Mylar, or Teflon. The filling tube may be constructed of a like material, with an interior diameter of about 1.0 mm and a wall thickness of about 0.5 mm.

Prior to inflation, a portion of the balloon is placed through the undilated or partially dilated cervix such that the distal end of the balloon extends into the uterine region, the proximal end with the inflation tube attached extends into the vaginal region, while the center portion passes into and remains inside the cervical region. Upon inflation with a fluid such as air, sterile water, or a sterile saline solution, the outside wall of the central portion presses radially against the cervix to induce ripening.

In another embodiment of the invention, the thickness of the balloon walls varies such that the proximal end and the distal end have wall thicknesses that are greater than the center section of the balloon. When the balloon is inflated, the central portion expands to a greater degree than the proximal end or distal end, thus applying more pressure on cervical region C as compared to the vaginal region or uterine region. Thus, excessive expansion of the distal end of the balloon into the uterus is reduced, alleviating potential problems for the pregnant patient and endangerment of the fetus.

In still further embodiments of the invention, the first end of the flexible inflation tube is fixed to the proximal end of the balloon. In other embodiments, the first end of the flexible tube extends into the proximal end of the balloon. Also contemplated are other embodiments wherein the first end of the flexible tube extends into the central portion of the balloon, or wherein the first end of the flexible tube extends into the distal end of the balloon.

DESCRIPTION OF ILLUSTRATIVE EMBODIMENTS

Figure 1:
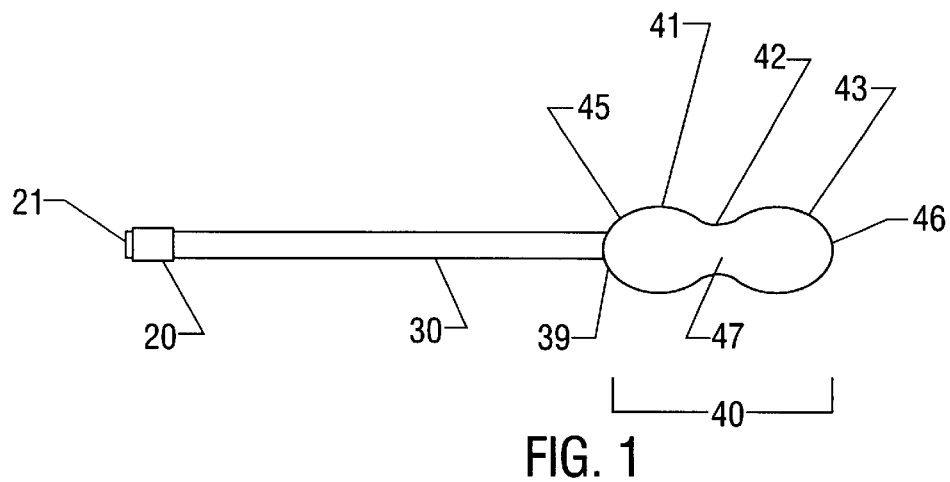
FIG. 1 shows one form of the catheter constructed in accordance with the present invention.

Catheter 10 as illustrated in FIG. 1 comprises a slender, flexible tube 30 that is open at both the distal tube end 39 and the proximal tube end 21. Located on proximal tube end 21, valve 20 controls the passage of air or liquid through the proximal tube end 21 into catheter 10.

On distal tube end 39, a single chamber inflatable balloon is fixed such that fluid may pass through the open distal tube end 39 and into balloon 40. Balloon 40 is generally shaped to be longer than it is wide, with proximal end 41 and distal end 43 connected by central portion 42. Proximal end 41 is closest to open tube end 39 of tube 30. Center portion 42 of balloon 40 is generally narrower, or smaller in circumference compared to proximate end 41 or distal end 43. Distal end 43 of balloon 40 is located farthest from tube 30.

To inflate balloon 40, fluid (such as a sterile saline solution) is introduced into catheter 10 through valve 20 into proximal tube end 21. The fluid passes through tube 30, and exits tube 30 into balloon 40 through distal tube end 39. Deflation of the balloon occurs by releasing valve 20 and permitting the fluid to exit catheter 10 through open proximal tube end 21.

Figure 2:
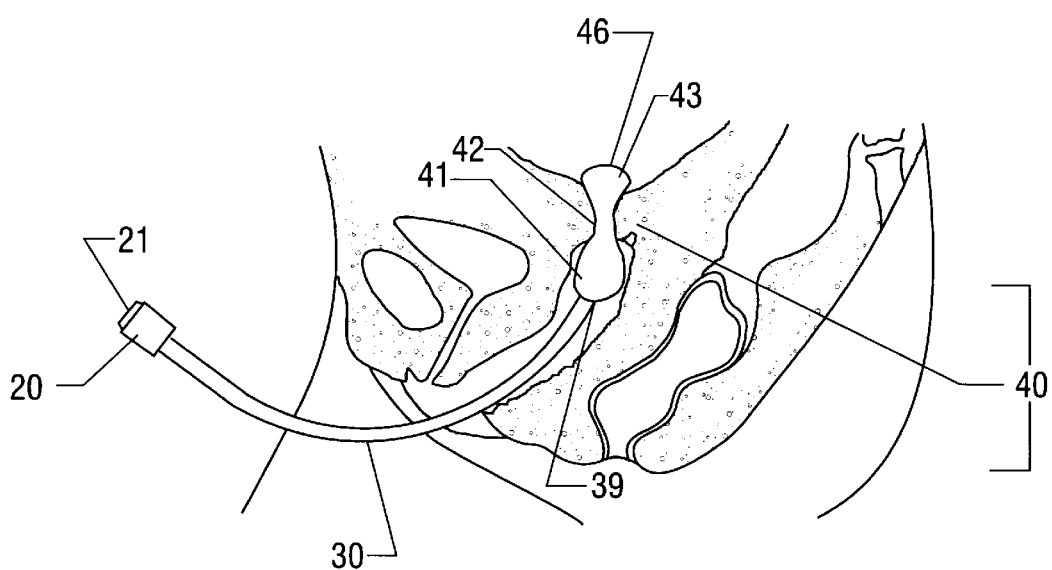
FIG. 2 is a diagram illustrating use of the catheter illustrated in FIG. 1 to induce labor and/or ripen the cervix.

FIG. 2 illustrates placement of catheter 10 in the cervical region for its use as a cervical ripening device. With balloon 40 deflated, catheter 10 is introduced into the birth canal of the female patient until balloon 40 is located within the cervical region C as shown in FIG. 2. Balloon 40 is at least partially inflated with fluid as described above such that distal end 43 is lodged in the upper region of cervix C and in the lower region of the uterus U, central section 42 is lodged in the cervical region, and proximal end 41 is lodged in the lower cervical region and in the vagina. If necessary, adjustments of the positions of the parts of balloon 40 should be made to apply adequate pressure to the appropriate areas for cervical ripening. Once in position, balloon 40 is partially inflated with an appropriate volume of fluid. Catheter 10 should remain in position until the onset of labor, until the cervix is maximally dilated by the catheter, or if spontaneous rupture of the membranes occurs. The device is inserted under direct visualization of the cervix after the vaginal walls have been retracted and the cervix has been sterilized with an appropriate antiseptic.

In another embodiment, balloon catheter 10 has a wall thickness that varies. For example, the walls of proximal end 45 and distal end 46 of balloon 40 may be thicker than walls 47 of central section 42. Upon inflation, central section 42 of balloon 40 would expand to a greater degree than proximal end 41 and distal end 43, thus applying more pressure on cervical region C as compared to the vaginal region or uterine region. Thus, excessive expansion of distal bulbous section 43 of balloon 40 into the uterus is reduced, reducing or preventing potential problems for the pregnant patient or endangerment of the fetus. Alternatively, only one end of the balloon, such as the distal end, may be of a greater thickness than the rest of the balloon. In this manner, excessive force against the uterine membranes is reduced or eliminated.

In another illustration of the balloon catheter 10, proximal end 41 of balloon 40 would expand more than distal end 43 of balloon 40 upon inflation. As a result, the danger of catheter 10 extending too far into the uterus may be minimized.

Finally, another embodiment that illustrates the utility of catheter 10 involves coating outer wall 47 of central section 42 of balloon 40 with a pharmaceutical product, which may be, for example, prostaglandin $E_2$. This feature would apply such pharmaceuticals to facilitate ripening of the cervix and inducement of labor. Thus, upon insertion and inflation of the balloon, a measured amount of pharmaceutical may be delivered to the cervical region.

REFERENCES

The following references, to the extent that they provide exemplary procedural or other details supplementary to those set forth herein, are specifically incorporated herein by reference.

Atad et al. "A Randomized Comparison of Prostaglandin, Oxytocin, and the Double-Balloon Device in Inducing Labor." *Obstetrics & Gynecology*, Vol. 87, No. 2, February 1996, pp. 223–26.

Atad et al. "Nonpharmaceutical ripening of the unfavorable cervix and induction of labor by a novel double balloon device." *Obstetrics & Gynecology*, Vol. 77, No. 1, January 1991, pp. 146–52.

James et al. Use of the Foley catheter as a cervical ripening agent prior to induction of labor." *International Journal of Gynecology & Obstetrics*, Vol. 47[/57], July 1994, pp. 229–32.

Kauff et al. "Intractable bleeding managed with Foley catheter tamponade after dilation and evacuation." Am. J. Obstet. Gynecol., Vol. 173, No. 3, Part 1, September 1995, pp. 957–58.

Onge et al. "Preinduction cervical ripening: A comparison of intracervical prostaglandin $E_2$ gel versus the Foley catheter." *Am. J. Obstet. Gynecol.*, Vol. 172, No. 2, Part 1, February 1995, pp. 687–90.

Rouben et al. "A Randomized Trial of Extra-Amniotic Saline Infusion Plus Intracervical Foley Catheter Balloon Versus Prostaglandin $E_2$ Vaginal Gel for Ripening the Cervix and Inducing Labor in Patients with Unfavorable Cervices." *Obstetrics & Gynecology*, Vol. 82, No. 2, August 1993, pp. 290–294.

Trofatter et al. "Cervical Ripening." *Clinical Obstetrics and Gynecology*, Vol. 35, No. 3, September 1992, pp. 476–86.

What is claimed is:

1. An improved balloon catheter for use in ripening a cervix prior to onset of labor, the catheter:
    (a) comprising a flexible tube with a first end a tip of the first end and a second end;
    (b) an inflatable balloon a proximal end and a distal end, wherein the proximal end of the balloon is attached at the tip of the first end of the tube, forming a fluid passageway into the balloon, the balloon having a shape generally longer than its width; the balloon further having a proximal end and a distal end shaped to be of a greater diameter than the diameter of a center portion of the balloon when the balloon is at least partially inflated; and
    (c) wherein the balloon is at least partially inflated by introducing fluid through the flexible tube into the balloon whereby the center portion of the balloon expands radially to apply pressure to the cervix and is of a lesser diameter than the proximal end and the distal end of the balloon throughout inflation.

2. The catheter according to claim 1, wherein the flexible tube includes a valve to regulate fluid flow through the tube.

3. The catheter according to claim 1, wherein the proximal end of the balloon inflates to a diameter larger than the diameter of the distal end.

4. The catheter according to claim 1, wherein the outer wall of the center portion of the balloon is coated with a pharmaceutical product.

5. The catheter according to claim 4, wherein the pharmaceutical product is prostaglandin $E_2$.

6. The catheter according to claim 1, wherein the proximal end of the balloon is attached to the first end of the tube and the tip of the first end of the tube extends into the proximal end of the balloon.

7. The catheter according to claim 1, wherein the proximal end of the balloon is attached to the first end of the tube and the tip of the first end of the tube extends into the central portion of the balloon.

8. The catheter according to claim 1, wherein the proximal end of the balloon is attached to the first end of the tube and the tip of the first end of the extends into a distal portion of the balloon.

9. An improved balloon catheter for use in ripening a cervix, the catheter comprising:
    a flexible tube having a first end and a second end;
    an inflatable balloon of a biocompatible material attached to the first tube end and forming a fluid passageway into the balloon the balloon having an inflated shape generally longer than its width, the balloon having a proximal end, a center portion, and a distal end;
    the balloon further constructed so that upon at least partial inflation, the diameters of the proximal end and the distal end are greater than the diameter of the center portion of the balloon;
    the balloon being inflated by passing fluid through the flexible tube and into the balloon; and
    wherein the thickness of the wall of the balloon at the center portion is less than the thickness at the proximal end and the distal end.

10. The balloon catheter according to claim 9, wherein the flexible tube includes a valve for regulating the fluid into the balloon.

11. The balloon catheter according to claim 9, wherein the proximal end of the balloon inflates to a diameter larger than the diameter of the distal end of the balloon.

12. The balloon catheter according to claim 9, wherein the center portion of the balloon is coated with a pharmaceutical product.

13. The balloon catheter according to claim 12, wherein the pharmaceutical product is prostaglandin $E_2$.

14. The catheter according to claim 9, wherein the first end of the flexible tube extends into the proximal end of the balloon.

15. The catheter according to claim 9, wherein the first end of the flexible tube extends into the central portion of the balloon.

16. The catheter according to claim 9, wherein the first end of the flexible tube extends into the distal end of the balloon.

17. A method of inducing labor comprising placing a balloon catheter according to claim 1 in the cervix such that the distal end of the balloon is located in the uterine region, the proximal end of the balloon is located in the vaginal region, the center portion of the balloon is in contact with the cervix, and the balloon is at least partially inflated to cause increased pressure on the cervix from the center portion of the balloon.

18. The method according to claim 17, wherein the balloon is inflated with a liquid.

19. The method according to claim 17, wherein the thickness of the wall of the balloon is less at the center portion than the thickness at the proximal end and the distal end.

* * * * *